United States Patent [19]
Wallace et al.

[11] Patent Number: 4,865,044
[45] Date of Patent: Sep. 12, 1989

[54] TEMPERATURE-SENSING SYSTEM FOR CATTLE

[76] Inventors: Thomas L. Wallace; Sheryl A. Wallace, both of 744 Calle Alta Mira, Santa Fe, N. Mex. 87501

[21] Appl. No.: 23,402

[22] Filed: Mar. 9, 1987

[51] Int. Cl.[4] .............................................. A61B 5/00
[52] U.S. Cl. .................................... 128/736; 128/903; 340/573; 340/870.17
[58] Field of Search ............... 128/736, 738, 903, 631; 340/573, 539, 870.16, 870.17; 119/1

[56] References Cited

U.S. PATENT DOCUMENTS

| | | | |
|---|---|---|---|
| 3,070,773 | 12/1962 | Woolston et al. | |
| 3,774,594 | 11/1973 | Huszar | 128/903 X |
| 3,781,837 | 12/1973 | Anderson et al. | |
| 3,972,320 | 8/1976 | Kalman | 128/903 X |
| 4,075,632 | 2/1978 | Baldwin et al. | |
| 4,411,274 | 10/1983 | Wright | 128/903 X |
| 4,471,354 | 9/1984 | Smith | 128/903 X |
| 4,618,861 | 10/1986 | Gettens et al. | 128/903 X |

OTHER PUBLICATIONS

Botsch et al, "Current Methods of Temperature Telemetry . . . ", Biology & Medicine, vol. 3, pp. 21-29, 1963.
Decker et al, "Completely Implantable . . . System", Proceedings . . . Rocky Mt. Eng. Symp, vol. 9, May 1972, pp. 133-137.
Kingma et al, "Wireless Fever Alarm Device", Med & Biol. Eng. & Comput., 1979, 17, 550-552.
Pauley et al., "A Microminiature Hybrid . . . System", Biochemistry Patient Monitg 8: No. 3, 83-172 (1981).

Primary Examiner—Lee S. Cohen
Attorney, Agent, or Firm—Skjerven, Morrill, MacPherson, Franklin & Friel

[57] ABSTRACT

Disclosed is a device for detecting temperatures which differ from a variable norm of particular use in detecting elevated temperatures in cattle. The device, one being attached to each animal, includes a square wave generator, an identification number encoder for outputting the identification number of the particular animal in the herd, a fever detector with an ambient temperature compensating circuit which provides output only when internal temperature of the animal is above a preset value for a given ambient temperature, and a transmitter which sends the identification code to a receiver. In certain embodiments, no separate fever detector is provided; rather the square wave generator outputs a frequency-modulated signal related to the internal body temperature.

Of particular interest is the identification number encoder which intermittently outputs a preset hardwired identification code to the transmitter at periodic intervals for transmission to a receiver either at constant intervals or when temperatures sensed by a temperature detector exceed the variable norm by a preset given amount.

15 Claims, 8 Drawing Sheets

TEMPERATURE-SENSING SYSTEM FOR CATTLE

BACKGROUND OF THE INVENTION

1. Field of the Invention

The disclosed invention relates to devices for the measurement of elevated temperatures and/or fevers in animals, particularly cattle.

2. Prior Art

For quite some time there has existed an unsolved need to determine when farm animals are sick without having to inspect each animal manually at regular intervals. Since a high percentage of sick animals have detectable fevers, an effective way of identifying such animals is to measure the body temperature of all the animals and to look for abnormally high temperatures. Although multiple schemes to monitor automatically the health of animals have been pursued by various companies, inventors, and research laboratories, each scheme eventually proved itself to be either uneconomical, unworkable, or both.

The detection of fever in animals can pose a special problem due to the fact that the normal, healthy internal temperature of an animal may vary with ambient temperature. In addition, of course, a device for detecting a fever in an animal must be small, inexpensive, have a reasonable operational life, with low power consumption, and have a useful transmission range.

U.S. Pat. No. 3,070,773 issued to Woolston, et al. describes a device which transmits ambient temperature information as well as internal temperature information using a frequency-modulation technique. The described device, although useful in circumstances such as those for which the present invention is designed, requires an uneconomical, large amount of power because it is always powered up and active when an individual signal such as the internal temperature signal is present. It does not directly indicate the presence of a fever in the cow because it does not account for or indicate changes in fever temperatures when ambient temperatures are high. Further, the disclosed system does not provide any means of identifying which particular animal in a large herd is the one with the fever.

U.S. Pat. No. 3,781,837 describes a device which transmits an alarm when an individual cow in a herd has a fever. The device described has a thermistor-based ambient temperature compensating circuit so that an alarm is triggered only when the internal temperature is about 40° C. when ambient temperatures are below about 38° C., or above 0° C. when ambient temperature is above about 38° C. However, this device continuously monitors temperature and generates a continuous alarm signal when an alarm condition is sensed; as a result, it continuously draws power and utilizes such a large amount of power that it is not economical. Again, such a device does not provide an automatic means for identifying which particular animal in a herd is the one with the fever.

U.S. Pat. No. 4,075,632 describes a device which acquires the energy to take a temperature reading only upon receipt of radiation emitted from an "interrogator"; it is not battery powered and does not operate independently of the separate interrogator. When the device is energized it transmits a temperature reading but does not compensate for the increase of internal temperature due to increased ambient temperature. Although it does provide identification number encoding which makes it clear which animal is emitting the signal, the method of powering the device with the "interrogator" limits the transmitting range of the devices to where they are of little practical use. In addition, the complexity and amount of circuitry in the devices makes the system prohibitively expensive.

Because other previous schemes have used infrared or sound to communicate temperature information or the health of an animal, either human observers have had to be present to hear the alarm or the infrared beam could only be received when the animal had its head in a given orientation.

SUMMARY OF THE INVENTION

This disclosed invention involves the workable solution of transmitting a long range radio frequency wave which can be automatically received regardless of orientation or obstructing objects. Where previous schemes have attempted to power the devices remotely in an attempt to reduce the cost per service hour, this invention prescribes a workable, battery-powered circuit that has a very long service life and low cost per service hour. Where other schemes with short device lifetimes have attempted to monitor and transmit continuously, this invention provides a means whereby a multiplicity of devices can transmit powerful signals on the same frequency without reducing device lifetime or interfering with each other. Most importantly, where in previous schemes the necessity of transmitting a signal, identifying the transmitter, or monitoring temperature have severely degraded operational life and drastically increased system cost, the functioning of this transmitter, fever sensor, and battery are actually enhanced by the inclusion of the identification encoder.

In accordance with one embodiment of the present invention a device is implanted in the ear and/or attached to the ear canal of an individual animal which device includes a clock signal generator, means for modulating an identification code onto the clock signal, means for detecting ambient and internal temperature together with means for transmitting a signal only when internal temperature is elevate and means for transmitting the identification code when the internal temperature is elevated. The signal is transmitted to an appropriate receiver for receiving and displaying the identification code transmitted.

The means for generating a clock signal is usually a low power, battery-powered square wave generator, most preferably based on an Intersil 7555 CMOS device or similar device.

The means for modulating an identification code onto the clock signal is usually an encoder. One possible encoder involves a first multi-bit counter receiving the clock signal from the square wave generator and outputting signals to the selected input lead of a multiplexer whose data input leads are hardwired with the identification code. One output signal is sent to the clock input lead of several cascaded counters which receive input signals from each other via the ripple carry-out lead channel. The ripple carry-output of the last counter is fed into the inhibit input lead of the multiplexer so that the multiplexer outputs the identification code followed by long periods when its output signal is inhibited. The effect of adding these cascaded counters is to limit the portion of time the encoder outputs the identification code thereby reducing power consumption by disabling the power consuming transmitter and fever detector circuits. In the preferred embodiment, the encoder includes four 74HC163 4-bit counters and one CD4051 8 to 1 multiplexer, and the embodiment in another aspect includes the encoder alone, apart from the remainder of the device.

A thermistor and op amp-based fever detector preferably constitutes the means for detecting ambient and internal temperatures when an elevated temperature is detected. The fever detector preferably includes two thermistors with sharp negative temperature coefficients of resistance, one located in the ear to sense internal body temperatures, and one exposed to ambient temperatures to sense increased ambient temperatures. The two thermistor circuits are active op-amp circuits. Above a certain ambient temperature, an identification code will be transmitted only with an internal temperature elevated above the internal temperature that would otherwise signal a fever condition.

The device also includes a radio frequency transmitter for transmitting the signal to a receiver/decoder unit; preferably the transmitter is a common oscillator circuit transmitter with a tunable tank circuit.

The second embodiment of the invention lacks the fever detector described above, and instead includes only one temperature variable resistive element, usually a thermistor, which forms a portion of the square wave generator which is itself placed in the inner ear of the cow. Thus, the square wave produced by the square wave generator has a frequency related to the temperature of the inner ear of the individual cow. The encoder generates an identification code using this square wave. The output signal of the encoder modulates a transmitted radio wave which is sent to an appropriate receiver/decoder unit. (The decoder may itself contain a highly accurate square wave generator for use as a standard to measure the frequency of the received square wave; when the frequency changes sufficiently to indicate that a fever condition exists, the identifying code can be displayed.) In contrast to the first embodiment, this circuit periodically transmits an identification number regardless of ambient temperature.

This embodiment of the invention is sensitive enough to detect mild changes in temperature due to changes in the ovulation cycle in addition to actual fever conditions. It can also detect when the inner ear sensor has fallen out of the ear. If a sensor has fallen out of the ear, the sensor would be exposed to ambient temperature. A received square wave whose frequency corresponds to ambient temperature would then indicate such a dislodged sensor. It should be noted that with this embodiment of the invention compensation for ambient temperature is performed after the transmissions are received at the receiver.

Added benefits of this embodiment of the invention are that the extra fever detector circuitry is not included in the multiple devices attached to individual animals, reducing the cost of the system. In addition, the cost of individually calibrating each fever detector device and the possibility of decalibration are eliminated by eliminating the fever detector portion of the telemeters.

DETAILED DESCRIPTION OF THE SPECIFIC EMBODIMENTS

Figure 1:
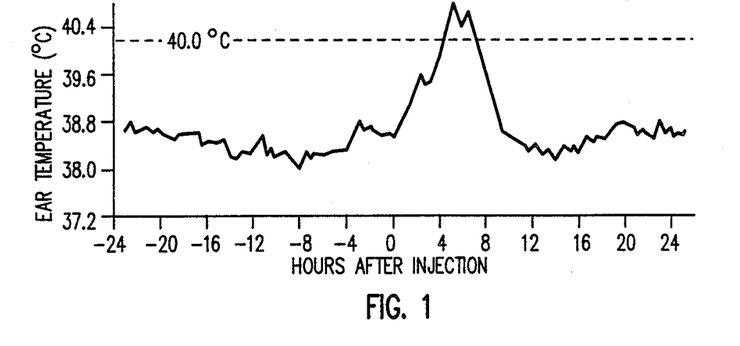
FIG. 1 is a graph illustrating internal temperature measured in the internal ear of a cow plotted against time after injection of tuberculin.

As discussed above, it is necessary in the maintenance of herds of cattle to detect when one or more animals in the herd have developed an illness in order to treat and/or remove them from the herd and reduce the possibility of contagion. One way of determining when an animal is ill is the presence of a fever which will appear in the animal after initial exposure to the virus or bacteria causing the infection. FIG. 1 illustrates the internal ear temperature of a cow before and after injection of tuberculin and shows a rise in temperature to fever level between about four and eight hours after injection.

Under ordinary circumstances, an internal temperature of 40° C. or 104° F. indicates a fever and illness although studies have shown that if ambient temperature increases, normal internal cattle body temperature also increases so that an internal temperature of about 40° C. does not constitute a fever when the ambient temperature is above about 38.5° C. Thus, the internal body temperature of a sick animal when outdoor temperatures are high will be increasingly high; correspondingly, internal temperatures indicative of illness at lower ambient temperatures do not indicate illness when outdoor temperatures are high. Thus, the present invention can with advantages provide means for compensating for increased internal temperatures of healthy animals with increased ambient temperatures.

Figure 2:
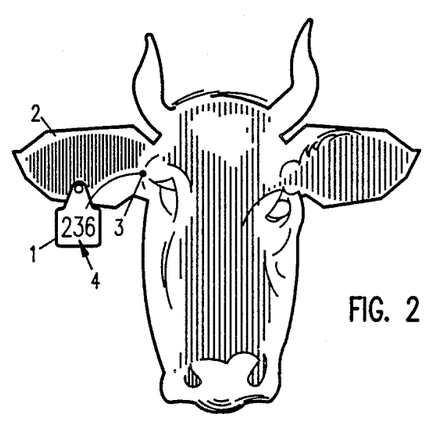
FIG. 2 is a view of the entire device of the present invention in use.

Referring now to FIG. 2, the present invention includes a multiplicity of individual devices each fixed to one cow. The device 1 is small, approximately 3"×3" in the case of the first embodiment of the invention and approximately 2"×2" in the case of the second embodiment of the invention, and is attached to the cow's ear 2 as if it were an earring, being small enough not to distract the cow or cause problems. The device includes a probe 3 extending into the internal ear for exposure to the internal body temperature of the cow; in the case of the first version of the invention including the fever detector, an additional probe not specifically shown in FIG. 1 is provided on the surface of tag 1 for exposure to ambient temperature. In addition, an identification number 4 (here the number "236") encoded in the device is also imprinted on the surface of tag 1 for easy location of an animal with a particular encoded number.

Figure 3:
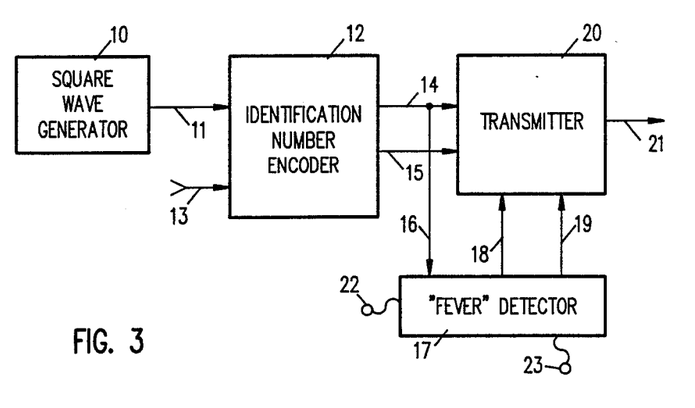
FIG. 3 is a schematic diagram of the first embodiment of the device with a fever detector.

Referring now to FIG. 3, a schematic outline of the preferred embodiment of the present invention can be seen. The invention includes a square wave generator 10 with output lead connected to an identification number encoder 12 hardwired 13 with an identification code and providing output lead 15 which carries a signal representing the identification code directly to transmitter 20 and output lead 14 which carries power, only to a fever detector 17 with two thermistors 22 and 23 exposed to internal and ambient temperatures respectively. Fever detector 17 outputs power on lead 18 to transmitter 20 and a fever signal on lead 19 to transmitter 20 as well.

In operation, square wave generator 10 sends a square wave signal to identification number encoder 12 which amplitude-modulates the square wave to intermittently periodically send an identification code in the form of a two-bit signal for synchronization followed by a six bit identification code to a NAND gate of transmitter 20. For the duration of time that the identification code is sent to the transmitter 20, the identification number encoder powers the transmitter and fever detector circuits by sending a power signal to an NPN-PNP transistor circuit. If during this time, the internal temperature of the animal, as compared to the ambient temperature, is sufficiently high, fever detector will send a high signal to the same NAND-gate of transmitter 20. When both NAND-gate input signals are positive and the transmitter is powered up, the identification code is transmitted on a radio wave to a receiver for use and evaluation. When the identification code is not being sent to the transmitter, the fever detector is not powered and no transmission is possible.

Figure 4:
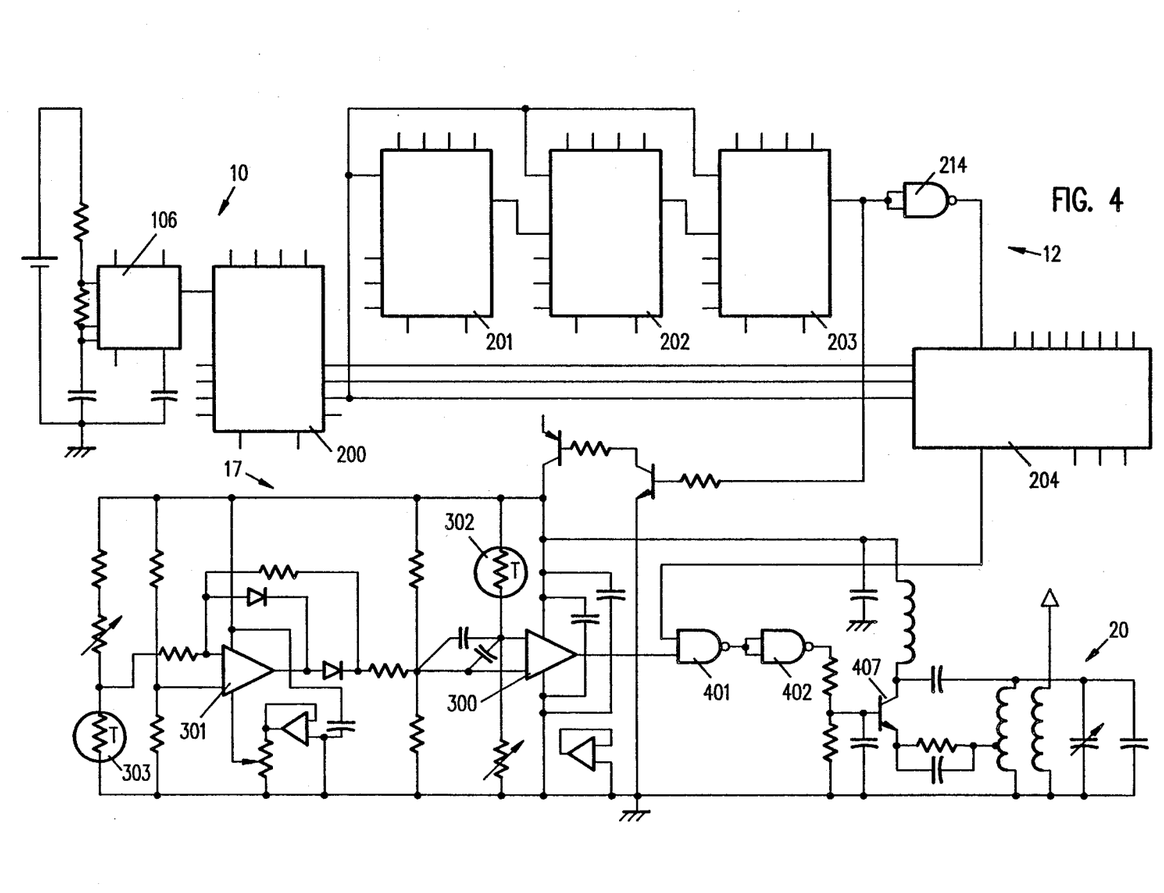
FIG. 4 is a overall circuit diagram of the first embodiment of the present invention.
Figure 5:
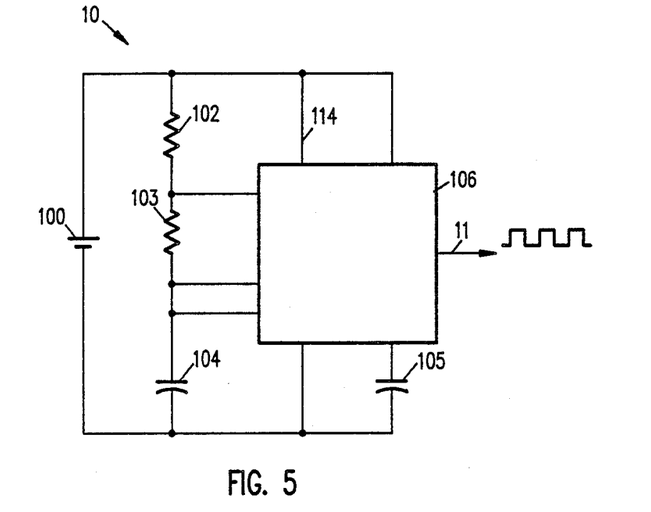
FIG. 5 is a circuit diagram of the preferred square wave generator of the present invention.

Referring now to FIGS. 4 and 5, the preferred square wave generator of the present invention is illustrated in detail. Square wave generator 10 is powered by one 3.0 volt lithium battery 100 parallel with two 2.2M ohm resistors 102, 103 and a 100 pF capacitor 104 plus an 0.01 uF capacitor 105 connected between CMOS device 106 and ground. The circuit powers an Intersil 7555 CMOS device 106 to produce square wave output 11.

Although many low power CMOS devices can be used in the square wave generator of the present invention, the Intersil 7555 CMOS structure above was selected because it requires less than 50 nA supply current. Because this portion of the circuit never powers down, it uses more power than any other component in the entire unit and a low-power structure such as a CMOS device is with advantage used. Since the 7555 CMOS device will operate down to a two volt supply voltage, it is more than compatible with the three volt power supply utilized in the preferred embodiment; in addition, it is desirable because it is relatively resistant to temperature variations. In the preferred embodiment the square wave generator and its associated resistor/capacitor network operates at 2.2 kHz and uses 0.048 mA current.

The circuit described, however, can be scaled to accommodate any supply voltage from about 3.0 volts to about 25 volts. It appears that batteries are the best energy source to power the generator, but the selection of particular battery sources will of course depend on the supply voltage desired, and the particular needs to be served by the system. For a given size and weight of the battery, high battery voltages such as 6.0 volts or more are preferable if a high-transmission range is desired; low battery voltages such as the 3.0 volt supply voltage shown in the preferred embodiment, on the other hand, extend battery life.

Figure 6:
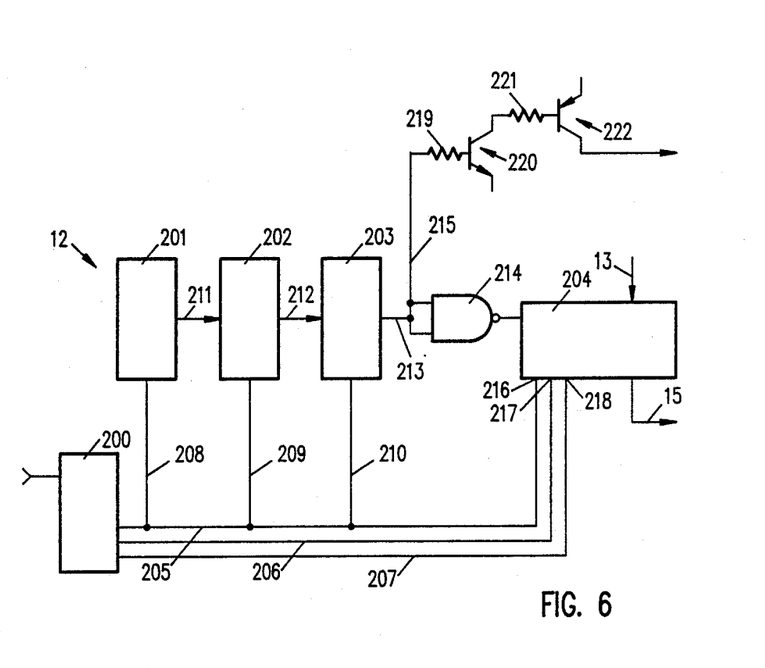
FIG. 6 is a circuit diagram of one possible identification number encoder of the present invention.

Referring now to identification number encoder 12 shown in FIGS. 4 and 6, the clock signal is output from square wave generator 10 and fed into the clock signal input lead of one of four 74HC163 four-bit counters 200, 201, 202, 203. The three lowest outgoing bits are input via conductors 205, 206 and 207 into select input leads 216, 217 and 218 of an eight-to-one CD4051 multiplexer 204 having an eight-bit hardwired code at 13, the first bit being a "one" and the second bit being a "zero" for synchronization with a receiver, and the remaining six bits constituting the identification code for the individual animal.

The Q3 output signal of the initial counter is also input in parallel via conductors 208, 209 and 210 to the clock signal input lead of three additional four-bit counters 201 through 203. The output signal from the first counter 201 via the ripple carry output is fed into the PE input lead of the next counter 202 and then into the final counter 203 via conductors 211 and 212, resulting in division of the output two to the twelfth times. The output signal from counter 203 is fed into 74HC00 NAND gate 214 and is inverted to be input into the inhibit input lead of multiplexer 204. This output signal from counter 203 is also sent via conductor 215 into an NPN-PNP transistor circuit including 10M ohm resistor 219, transistor 220, 82K resistor 221, and transistor 222 in series to power the fever detector 17. Preferred transistors 220 and 222 are types 2N3904 and 2N3906, respectively. The output signal of the identification code goes directly from multiplexer 204 via conductor 15 to transmitter 20.

An important difference between this encoder and other encoders is the addition of the counters. For a very low cost, the counters simultaneously keep power consumption to a minimum and enable multiple transmitters to transmit on one frequency. Counters are preferred to other timing elements such as multivibrators because additional discrete timing resistors and capacitors need not be added.

In operation, the input signal into the inhibit line of the multiplexer disables the multiplexer for a given period of time; in the present embodiment, the multiplexer output signal is disabled for a period of 15 seconds after output of the identification code. The relative periods of enablement and disablement of the multiplexer can be adjusted by adding more counters; if additional four-bit counters are added in series with counters 201 through 203 to receive and divide the Q3 output further, the multiplexer will be disabled for a longer period relative to the enablement period. (In the embodiment shown, output is divided two to the twelfth times; addition of another four bit counter will divide it 2 to the 16th times and so forth.) In order to increase the number of cattle that can be identified (the present six bit system described in the current embodiment will identify approximately 64 cows), a larger code must be hardwired into the multiplexer; furthermore additional select input signals may need to be activated to power the multiplexer and counters larger than four bits may be required.

Figure 7:
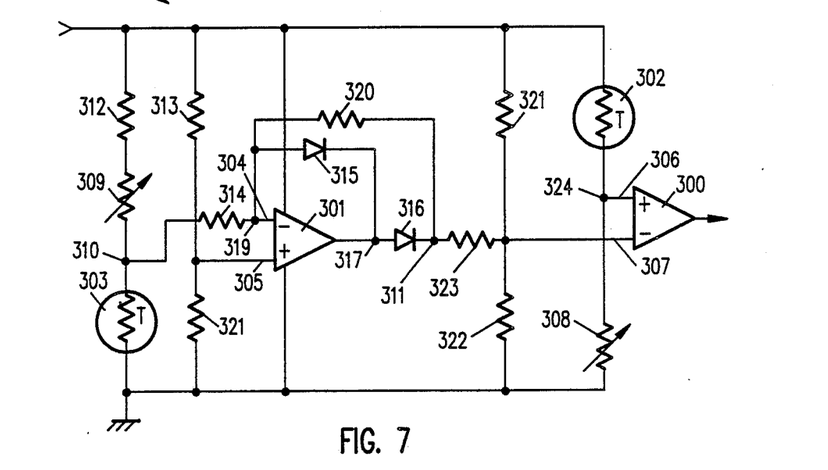
FIG. 7 is a circuit diagram of the preferred fever detector of the present invention.

Turning to FIGS. 4 and 7, the preferred fever detector of the present invention is based on two thermistors 302 and 303 and two op amps 300 and 301, preferably National Semiconductor LM10C low-power op amps.

Thermistor 302 is placed in the inner ear of the cow, the voltage of node 324 between thermistor 302 and variable resistor 308 controlling the positive input signal 306 into op amp 300. Op amp 300 sends a fever signal when the voltage at the positive input lead is greater than the voltage at the negative input lead. Negative input signal to op amp 300 is received from reference node 311. This value is adjusted by the ambient temperature compensating portion of the circuit based on thermistor 303 and op amp 301. Ambient temperature thermistor 303 together with 100K variable resistor 309 and 47K resistor 312 control the voltage of node 310 which a feeds negative input signal into op amp 301. As temperature increases, the voltage of the node decreases, together with the input signal into negative input 304 of op amp 301 received from node 310 via 100K resistor 314. Diode 315 comprises one negative feedback loop of op amp 301. The series connection of diode 316 and 100K resistor 320 comprise the second negative feedback loop of op amp 301. The output from the op amp 301 circuit adjusts the voltage of reference node 311 through 68 K resistor 323, thus controlling the input signal into negative input 307 of op amp 300.

The output signal from op amp 301 maintains the voltage of its positive input signal unless the positive input signal is above the negative input signal, in which case it rises above the voltage of the positive input signal by the amount that the negative input signal is below the positive input signal. In effect, thus, op amp 301 and its two negative feedback loops do not affect the voltage at reference node 311 until ambient temperature reaches about 38° C. A continued increase in the temperature of thermistor 303 causes an increase in the voltage of reference node 311 and an increase in the negative input signal of op amp 300. Output from op amp 300 signaling the existence of a fever is triggered when the input signal at node 306 from internal temperature thermistor 302 and associated resistor 308 exceeds the negative input signal. The predetermined voltage of the positive input signal 306 at a given inner ear temperature is adjusted by calibrating variable resistor 308. Calibration of variable resistor 309 in the ambient temperature compensating circuit is required in order to fix the "trip" temperature at which the negative input signal to op amp 301 falls below the positive input signal.

An LM10C National Semiconductor op amp was chosen to be the active element in the preferred fever detector network because it operates down to a 1.1 volt supply voltage and uses a supply current of only 270 microamps. Device 300 could be either a comparator or an op amp.

As to thermistors, they are the preferred temperature sensitive current regulating devices due to their low cost, hardiness, sensitivity to temperature and large negative coefficients of resistance. The preferred thermistors are high resistance thermistors such as Victory Engineering Corporation 51A11 glass bead probe thermistors with a resistance at 25° C. of 100K plus or minus 15%. Linearity is not a major concern for the thermistors used; for the internal ear thermistor, no linearity at all is necessary since the thermistor is used only to set a trap point and must have a consistent value only at a high temperature of about 40° C. Linearity is not a major concern for the thermistor monitoring ambient temperature because it needs only to raise the reference voltage of the cow ear op amp over about a 10° C. range.

As indicated above, both of the thermistor bridge circuits in the fever detector require calibration to fix the trip points at which the op amps signal. The easiest way to provide such calibration is by the addition of variable resistors such as 308 and 309; fixed resistors cannot easily be used (because thermistors are not typically interchangable) due to inherent variability of thermistor resistance at a given temperature.

In operation, thus, the ambient temperature compensating circuit in the fever detector adjusts the negative input signal into op amp 300 according to the ambient temperature. It does not adjust the voltage of node 311 when ambient temperature is below a certain temperature (about 38° C.), but it does increase the voltage of node 311 when ambient temperature rises above that point. The internal ear thermistor circuit provides a positive input signal into op amp 300, and a signal indicating presence of a fever is output when the positive input voltage exceeds the negative input voltage. Adjustments of variable resistor 308 are made to calibrate the internal ear thermistor circuit to adjust the temperature at which op amp 300 outputs a fever signal at a given ambient temperature. Similar calibration of variable resistor 309 in the ambient temperature circuit adjusts the temperature at which the ambient compensation circuit begins adjusting the voltage of node 307.

Figure 9:
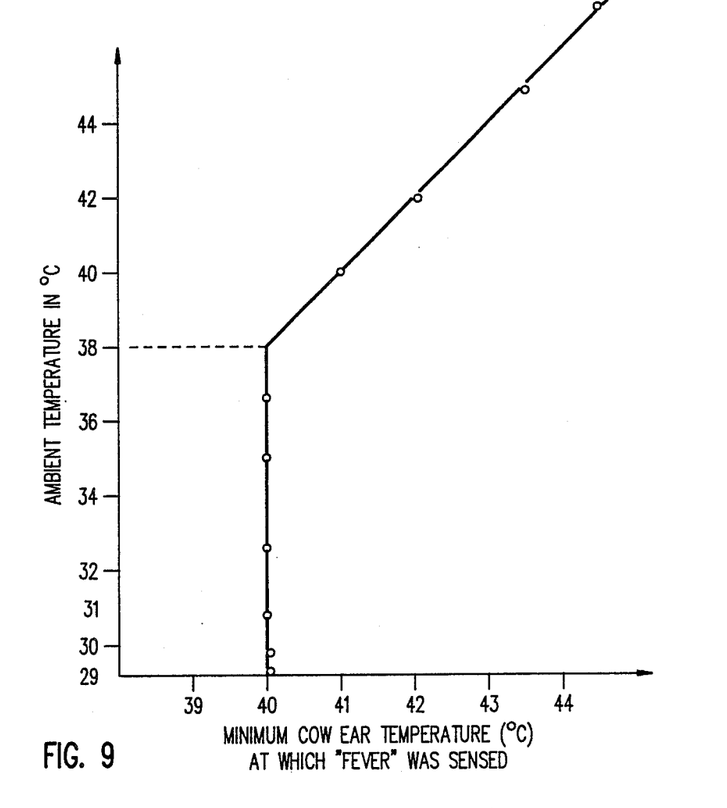
FIG. 9 is a graph of the internal temperature at which alarm transmission is triggered for ambient temperatures in the range from 29° C. to 44° C.

FIG. 9 illustrates the function of the ambient temperature compensating circuit in the cow ear fever detector. Ambient temperature in degrees centigrade is illustrated on the Y axis and internal temperature in degrees centigrade at which a fever signal is transmitted is shown on the X axis. As shown, in the preferred embodiment, a fever signal was emitted at 40° C. for ambient temperatures below 38° C.; at ambient temperatures above 38° C., the signal was emitted at temperatures above 40° C. by an amount proportional to the amount ambient temperature was above 38° C.

The invention also includes a transmitter to transmit the identification number to a receiver when the animal is in a fever condition. Common short range transmitter oscillator circuits such as Colpitts, Hartley, or Pierce oscillators can be used. For cost reasons, tunable tank circuit oscillators are preferred to crystal-controlled oscillators. A power amplifier circuit could be added after the oscillator if added range is required for the application. The frequency of the transmitter signal should range anywhere from 25 MHz to 500 MHz because the transmitting antenna is located on the animal's ear and must be very small.

Figure 8:
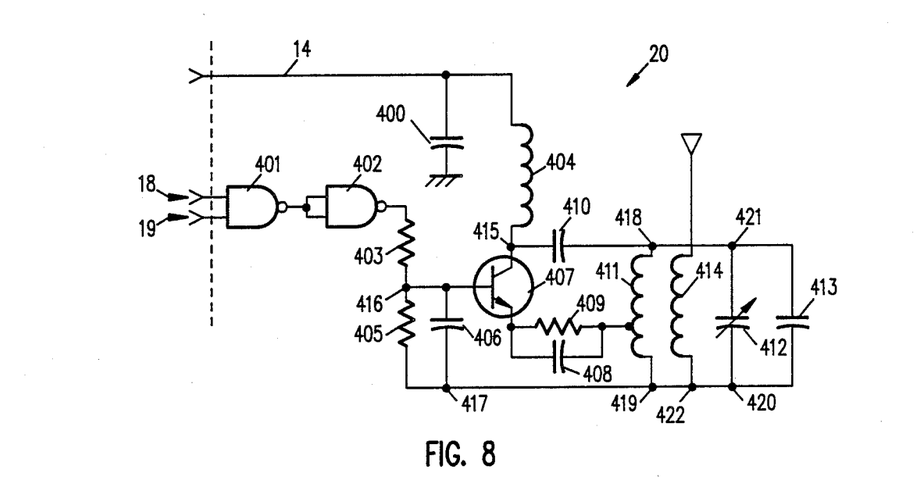
FIG. 8 is a circuit diagram of one possible transmitter of the present invention.

A preferred transmitter is shown in FIGS. 4 and 8; it is a Hartley oscillator tunable from 27-35 MHz; in operation, a 3.0 supply voltage and about 6.83 mA of current are required. Power is input to the transmitter directly from the counter output of the identification number encoder via conductor 14 and RFC coil 404 to node 415. A 22 pF mica capacitor is attached between conductor 14 and ground to node 415. A 0.01 micro F ceramic capacitor 410 and bipolar transistor 407, preferably of type 2N5943 are adjacent node 415. An input signal from the fever detector comes via conductors 18 and 19, providing the identification code and fever signal, respectively, to NAND gate 401 and subsequently to another NAND gate 402 (both preferably 74HC00 NAND gates). These are located in series with a 3.3K resistor 403 followed by node 416 adjacent the base of transistor 407. Beyond node 416 is another 3.3K resistor 405 in parallel with 0.01 micro F mylar capacitor 406 terminating at node 417. A 0.1 micro H coil between nodes 418 and 419 is in parallel with a 0–20 pF variable capacitor 412 between nodes 420 and 421 and in parallel with a 30 pF mica capacitor 413 to complete the exterior transmitter circuit. Antenna and coil 414 emanate from this circuit at node 422 between nodes 419 and 420. The emitter of transistor 407 is connected to a 41 ohm resistor in parallel with an 0.01 uF ceramic capacitor terminating in coil 411.

In operation, the transmitter is powered only a small fraction of the time. The current driving capability of the output signal of the four-bit counters of the identification number encoder is boosted via the NPN-PNP transistor pull-up circuit thereby enabling the identification number encoder to periodically power the transmitter and fever detector circuits. The transmitter transmits a signal when it is powered up and receives both a fever signal and an identification code signal at NAND gate 401, the incoming signals functioning to bias or ground transistor 407.

In connection with the present invention, an appropriate receiver can be used to receive the transmitted information indicating that a given animal has a fever. A standard radio receiver of any of a number of types now known and available built to receive signals at the frequency transmitted can be used. A specially designed decoder decodes the output signal of the standard receiver, determines if a valid transmission has occurred, and outputs valid transmissions as numbers on a display so that sick animals may be identified.

The above device was constructed on vector boards, utilizing one 3.0 volt lithium battery. Lead lengths were minimized to avoid problems resulting from aligning the unshielded transmitter adjacent an op amp circuit, capacitors were added where necessary to eliminate high frequency noise, and a shielded small diameter coaxial cable was used to attach the cow ear thermistor to the fever detector. The circuit performed as follows:

| | |
|---|---|
| Power Consumption | .054 milliamperes |
| Expected Battery Life | 2.1 years |
| Circuit Size | 3.0 square inches |
| Transmitting Range | 50 feet |
| Volume Manufacturing Costs (with Custom Integrated Circuit) | $8.00 |

Figure 10:
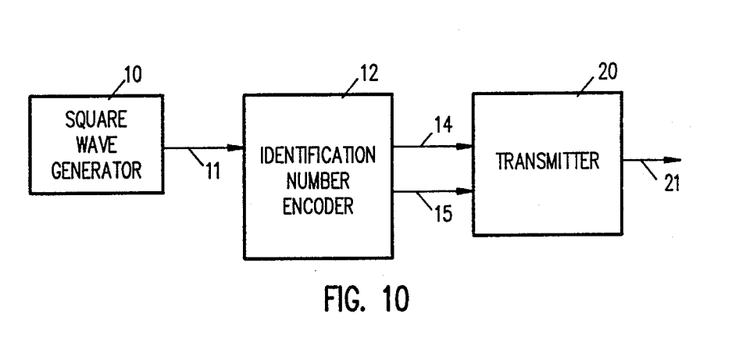
FIG. 10 is a schematic diagram of the second version of the present invention without the specialized fever detector.
Figure 11:
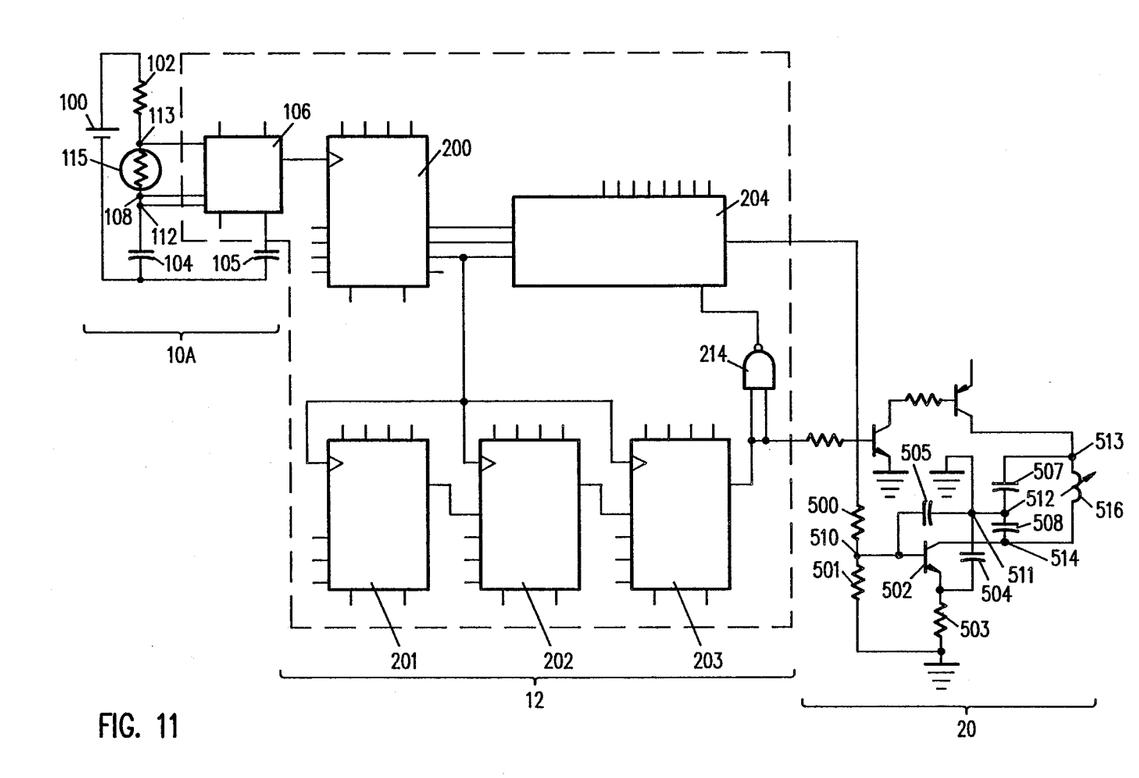
FIG. 11 is an overall circuit diagram of the preferred embodiment of the second embodiment of the invention lacking the fever detector.
Figure 12:
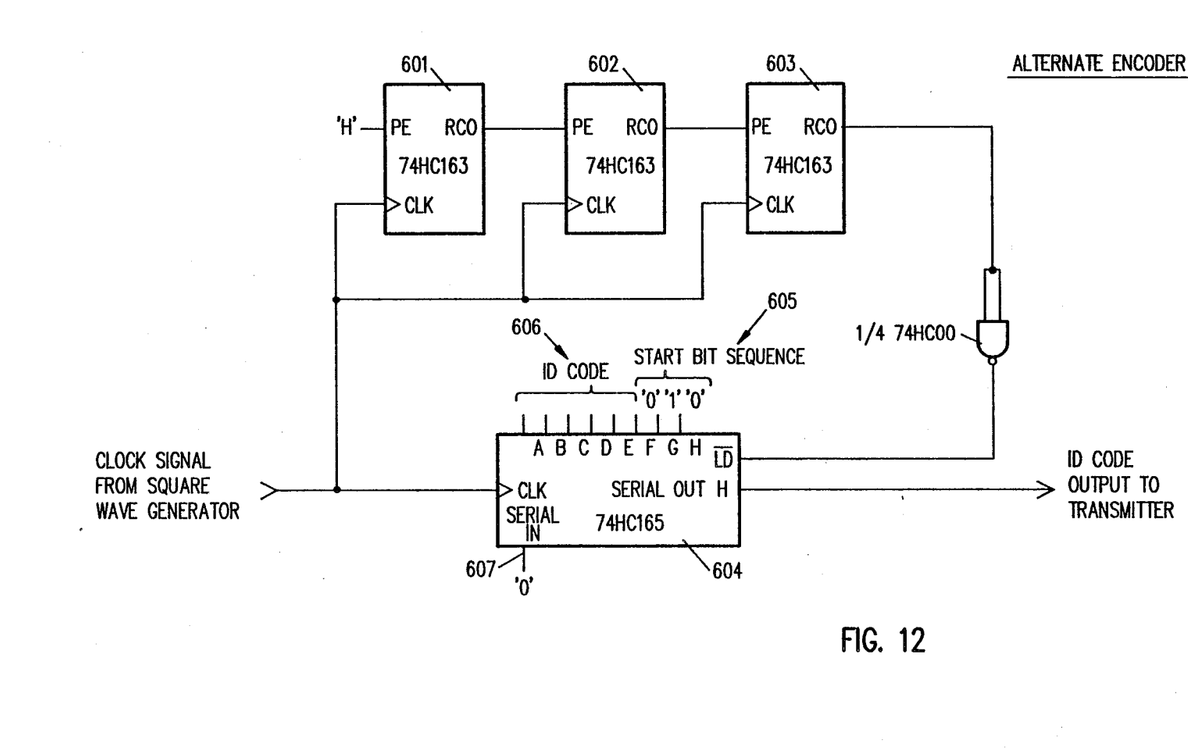
FIG. 12 is the alternate encoder.
Figure 13:
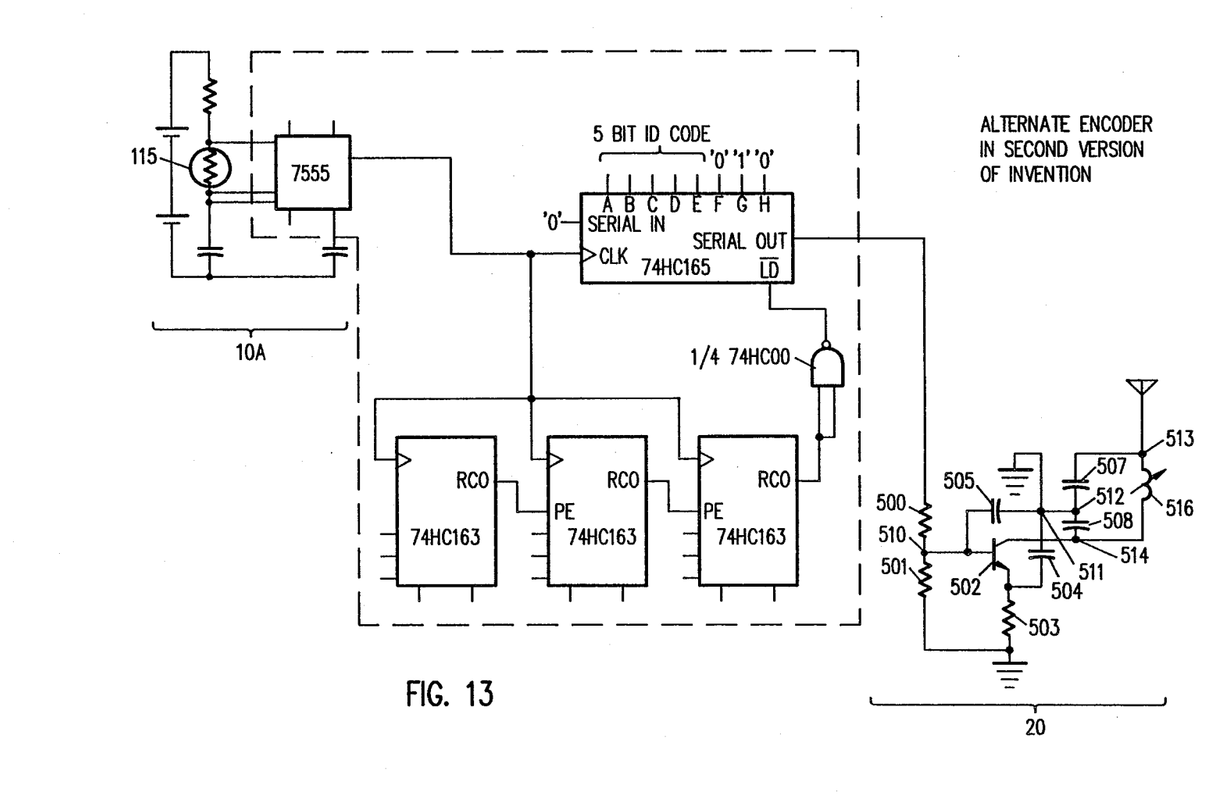
FIG. 13 is the alternate encoder in second embodiment of invention.

In the second embodiment of the invention (FIG. 10), no "fever detector" is necessary. For this version, two embodiments are shown using different encoders. The encoder used in the embodiment shown in FIG. 11 is very similar to the encoder previously described. The embodiment shown in FIG. 13 implements a slightly different type of encoder. Note that both encoders utilize low power CMOS counters to ensure that the output of the encoder does not activate the transmitter but for a very small portion of the time. For both embodiments, square wave generator 10A includes, instead of resistor 103, a thermistor 115 which is implanted in the internal ear of the animal. As a result, the frequency of the actual square wave generated by the square wave generator will be a function of the inner ear temperature and relatively constant for a healthy animal. The identification number encoder also will produce an identification code sequence amplitude-modulated onto the square wave signal.

Where the operation of the encoder used in FIG. 11 was described in the description of the first embodiment, the operation of the encoder used in FIG. 13 will be described here in the description of the second version. This encoder, shown in more detail in FIG. 12, operates by having several cascaded 74HC163 counters 601, 602, 603 divide the frequency of the clock signal from the square wave generator 10A. The ripple carry-out of the last counter 603 is used to momentarily parallel load the shift register 604 with a hardwired startbit sequence 605 and identification code 6. When the parallel load signal is deactivated, the start bit sequence and identification code is shifted out to intermittently activate and deactivate the transmitter. After the identification code has shifted through the shift register, a low signal is shifted in because the serial input 607 to the shift register is hardwired low. The low signal supplied to the transmitter disables the transmitter, conserves power, and enables other transmitters to communicate on the same frequency.

The output signal of the identification number encoder goes to a transmitter through a 56K resistor 500 followed by node 510 directly adjacent to the base of a bipolar transistor 502. The emitter of transistor 502 is in series with a grounded 2.2K resistor 503 and node 510 is also connected to ground via 27K resistor 501. The emitter is also in series with a 4 pF capacitor 504. Between node 510 and transistor 502, is node 515 in series with 39 pF capacitor 505 followed by two nodes 511 and 512, the latter between 39 pF capacitor 507 and 45 pF capacitor 508 in a circuit which receives power input at node 513 and is completed by a silver-plated brass slug 516 with 1½ turns. 45 pF capacitor 508 is connected via node 514 to transistor 502.

In operation, the transmitter outputs an amplitude modulated identification code whose bit rate is proportional to internal ear temperature. It should be stressed that this version of the invention does not measure body temperature. It measures changes in body temperature only. Because the devices are not calibrated to transmit a given bit rate at a given temperature, various devices of this version that are all at the same temperature will output different bit rates. An appropriately constructed receiver/decoder unit will store a given number of past bit rates for each device being monitored. Because the animals to be monitored will be inspected and assumed to be healthy when the devices are attached, a healthy bit rate will be recorded for each animal. If, in the future, the receiver/decoder were to receive a bit rate a given percentage higher than the healthy bit rate, the receiver would output the identification code of that device.

The major advantage of this particular device over the first version is that each individual device, lacking the fever detector, does not require the costly calibration necessary to make the ambient temperature compensating circuit function. It is also less expensive to produce because fever detector circuitry need not be included in the large number of transmitting units (rather additional circuitry can be put in a single unit receiver/decoder). Further, the device can monitor other, milder changes in body temperature such as cyclical changes due to ovulation and cannot become decalibrated. In addition, the receiver/decoder can incorporate other environmental conditions such as time of day, date, windspeed, and humidity into its decision whether or not to display a given device code. The necessity of deciding whether or not an animal is feverish is not a function burdening the power constrained telemeters as it was in the first version.

The estimated cost of producing this version of the present invention in volume is considerably less than that of the previously described version and the entire device can be produced at a size of about two inches square or even less if a customized integrated circuit is utilized. Power consumption, of course, is still low due to the use of a low power CMOS device in the square wave generator and because the encoder ensures that the remaining portions of the device are only intermittently not constantly powered. For both embodiments, it is estimated that with an 0.25 ampere-hour battery, the circuits will be completely functional for approximately six months. The estimated cost of producing this embodiment is as follows, with a custom integrated circuit:

| | | | |
|---|---|---|---|
| 1 | custom IC | 1x | 2.00 | $2.00 |
| 1 | 7555 square wave gen. | 1x | .50 | .50 |
| 1 | glass bead thermistor | 1x | .75 | .75 |
| 7 | ceramic capacitors | 7x | .05 | .35 |
| 1 | mica capacitor | 1x | .05 | .05 |
| 1 | high freq. trans. | 1x | .40 | .40 |
| 2 | cheap trans. | 2x | .20 | .40 |
| 6 | resistors | 6x | .02 | .12 |
| 1 | 9.0 V battery | 1x | .50 | .50 |
| 1 | printed circuit board | 1x | .75 | .75 |
| 1 | coaxial cable + battery holder | 1x | .30 | .30 |
| +1 | variable inductor | 1x | .15 | .15 |
| | | | | $6.27 |

It will be understood, of course, that the foregoing disclosure has described in detail only the preferred embodiments of the invention and that numerous modifications and alterations may be made therein without the departing from the spirit and the scope of the invention as defined in the following claims.

We claim:

1. An apparatus for sensing temperature changes in a body comprising:
    a battery-powered signal generator for generating a signal having a variable frequency;
    frequency modulating means for varying the frequency of the generated signal as a function of the level of the temperature of the body; and
    amplitude modulating means for modulating the amplitude of the generated signal in accordance with a predetermined identification code to thereby tag the generated signal with an encoded amplitude waveform which identifies the body.

2. The apparatus of claim 1 further comprising transmitting means for transmitting the generated signal with the encoded amplitude waveform tagged thereon to a remote data collecting station.

3. The apparatus of claim 2 further comprising power consumption limiting means, coupled to the transmitting means, for intermittently deactivating the transmitting means so as to limit the power consumption of the transmitting means over time.

4. The apparatus of claim 3 wherein the power consumption limiting means includes one or more digital counters for establishing the period of the deactivation of the transmitting means.

5. The apparatus of claim 1 wherein the frequency modulating means is not calibrated so as to cause a predetermined frequency of the generated signal to correspond to a predetermined temperature level.

6. The apparatus of claim 1 wherein the generated signal is a digital signal characterized by a bit rate and the frequency modulating means includes means for adjusting the bit rate of the generated signal and further wherein the amplitude modulating means includes means for causing the encoded amplitude waveform to have first and second levels representing binary digits.

7. An apparatus for sensing temperature changes in a body comprising:
    a battery-powered signal generator for generating a signal having a selectable frequency;
    amplitude modulating means for modulating the amplitude of the generated signal to impart an identification code onto the generated signal;
    frequency varying means for varying the frequency of the generated signal with the identification code modulated thereon as a function of the temperature of the body;
    a transmitter for association with the body;
    powering means for intermittently powering the transmitter; and
    signal providing means for providing to the transmitter the generated signal with the identification code modulated thereon and the selectable frequency determined by the temperature of the body when the transmitter is powered;
    wherein the transmitter transmits the generated signal with the identification code modulated thereon as received from the signal providing means.

8. The apparatus of claim 7 further comprising timing means, operatively coupled to the transmitter, for intermittently enabling the transmitter to transmit the generated signal in accordance with a predetermined timing scheme.

9. The apparatus of claim 8 wherein the frequency varying means includes a thermistor which may be positioned adjacent to the body.

10. The apparatus of claim 9 wherein the signal generator comprises a low-power CMOS generator.

11. The apparatus of claim 10 wherein the transmitter comprises a RF oscillator circuit.

12. The apparatus of claim 11 wherein the oscillator circuit operates in the frequency range of approximately 25 to 500 MHz.

13. A telemetry device for transmitting temperature data corresponding to temperature changes in a body, comprising:
    a digital signal generator for generating a digital signal having a variable bit rate;
    temperature change indicating means, coupled to the digital signal generator and responsive to temperature changes in the body, for changing the bit rate of the generated signal in response to a change of temperature in the body; and
    digital encoding means, coupled to the signal generator, for setting predetermined ones of the bits in the generated signal on or off in accordance with a predetermined identification code.

14. The telemetry device of claim 13 further comprising an indicia bearing tag located proximate to said digital encoding means and adapted for attachment to said body, wherein the indicia of the tag corresponds in a predetermined manner to the identification code so that the location of the tag indicates at least approximately the location of the digital encoding means.

15. The telemetry device of claim 13 wherein the digital encoding means includes a code setting means for establishing the identification code in parallel form and a digital multiplexer for converting the established identification code from parallel to serial form.

* * * * *